US010782875B2

(12) United States Patent
Juarez et al.

(10) Patent No.: US 10,782,875 B2
(45) Date of Patent: Sep. 22, 2020

(54) TOUCHSCREEN METHOD FOR MEDICALLY PRECISE MEASUREMENTS IN ULTRASOUND IMAGES

(71) Applicant: Emagine Solutions Technology LLC, Tucson, AZ (US)

(72) Inventors: Jose L. Juarez, Tucson, AZ (US); Courtney Williams, Tucson, AZ (US)

(73) Assignee: EMAGINE SOLUTIONS TECHNOLOGY LLC, Tucson, AZ (US)

( * ) Notice: Subject to any disclaimer, the term of this patent is extended or adjusted under 35 U.S.C. 154(b) by 0 days.

(21) Appl. No.: 16/656,408

(22) Filed: Oct. 17, 2019

(65) Prior Publication Data
US 2020/0125251 A1 Apr. 23, 2020

Related U.S. Application Data

(60) Provisional application No. 62/746,775, filed on Oct. 17, 2018.

(51) Int. Cl.
G06F 3/0484 (2013.01)
G06T 3/40 (2006.01)
(Continued)

(52) U.S. Cl.
CPC .......... G06F 3/04883 (2013.01); G06F 3/041 (2013.01); G06F 3/04845 (2013.01);
(Continued)

(58) Field of Classification Search
None
See application file for complete search history.

(56) References Cited

U.S. PATENT DOCUMENTS 4,833,625 A * 5/1989 Fisher ................. H04N 1/2179
345/536
8,016,758 B2 * 9/2011 Wu .......................... A61B 8/00
600/437
(Continued)

FOREIGN PATENT DOCUMENTS

CN 104622500 A 5/2015
GB 2359686 A 8/2001
(Continued)

OTHER PUBLICATIONS

D Jones, Smartphone-Compatible Ultrasound Probe, Journal of Diagnostic Medical Sonography, Jul. 2014, 30(4):200-204.
(Continued)

Primary Examiner — Yongjia Pan
(74) Attorney, Agent, or Firm — Nguyen Tarbet

(57) ABSTRACT

A method for taking medically precise measurements with a multi-touch input surface 206 having the steps of displaying, by a graphical user interface: a first point 101 on an ultrasound image 103, wherein the first point 101 is configured to translate with two dimensions of translational freedom upon actuation by a user, and a floating magnification window 102, wherein displaying the floating magnification window 102 comprises calculating a square frame based on the first point 101, a size of an area of magnification, a width of the multi-touch input surface 206, and a height of the multi-touch input surface 206, wherein the square frame is configured to crop a copy 104 of the ultrasound image 103.

20 Claims, 9 Drawing Sheets

Figure 2:
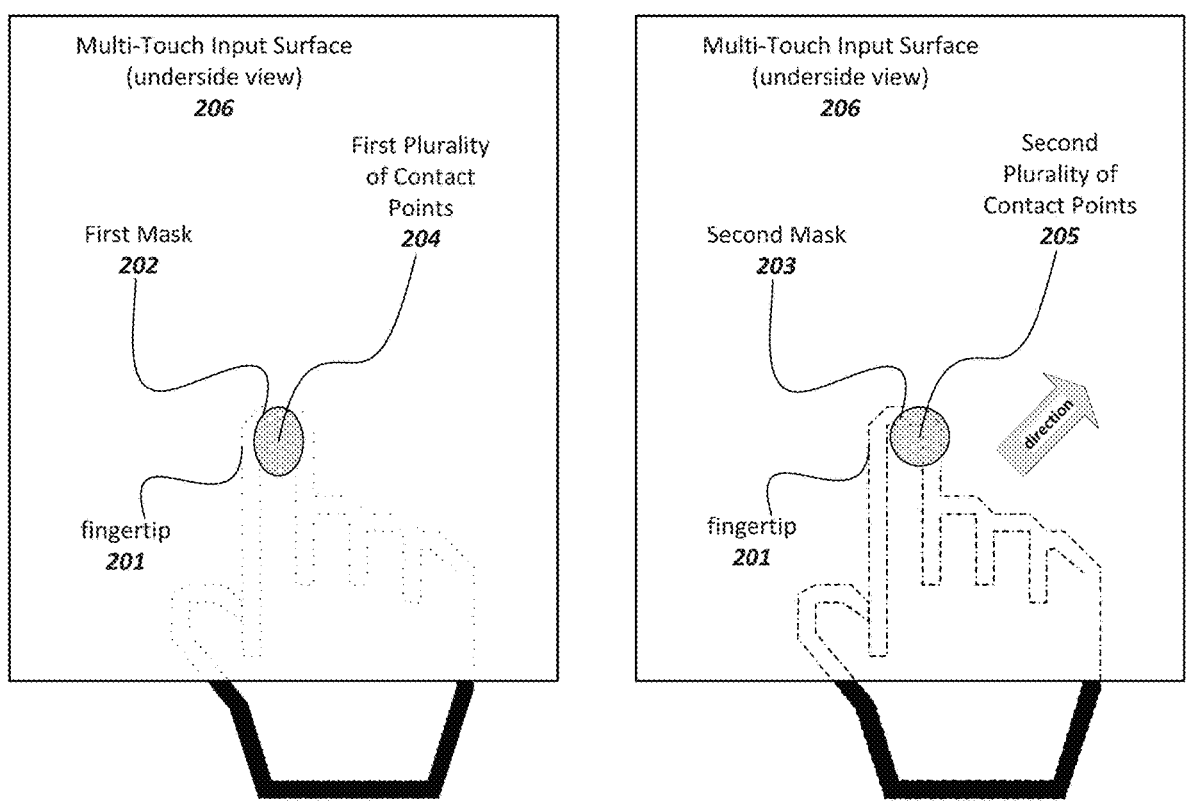

(51) Int. Cl.
*G16H 30/40* (2018.01)
*G06F 3/0488* (2013.01)
*G06F 3/041* (2006.01)
*G06T 3/20* (2006.01)
*G06T 7/60* (2017.01)

(52) U.S. Cl.
CPC .................. *G06T 3/20* (2013.01); *G06T 3/40* (2013.01); *G06T 7/60* (2013.01); *G16H 30/40* (2018.01); *G06F 2203/04104* (2013.01); *G06F 2203/04808* (2013.01); *G06T 2200/24* (2013.01); *G06T 2207/10132* (2013.01); *G06T 2207/20101* (2013.01)

(56) References Cited

U.S. PATENT DOCUMENTS

| | | | |
|---|---|---|---|
| 9,146,674 B2 * | 9/2015 | Karlsson | G06F 3/04883 |
| 9,607,570 B2 * | 3/2017 | Yoshimoto | G01C 21/367 |
| 2006/0242159 A1 | 10/2006 | Bishop et al. | |
| 2007/0013722 A1 | 1/2007 | Souza | |
| 2010/0298701 A1 * | 11/2010 | Shin | A61B 8/00 600/437 |
| 2011/0087651 A1 | 4/2011 | Westin et al. | |
| 2011/0128966 A1 | 6/2011 | Westin et al. | |
| 2013/0053657 A1 | 2/2013 | Ziarno et al. | |
| 2013/0249952 A1 * | 9/2013 | Kusakabe | G06T 3/40 345/671 |
| 2014/0142984 A1 | 5/2014 | Wright et al. | |
| 2015/0099968 A1 * | 4/2015 | Jamello | A61B 5/0066 600/425 |
| 2015/0286791 A1 | 10/2015 | Altobello et al. | |
| 2016/0042510 A1 | 2/2016 | Lttell | |
| 2016/0278739 A1 | 9/2016 | Pelisser et al. | |
| 2016/0350503 A1 * | 12/2016 | Jun | A61B 8/54 |
| 2017/0090571 A1 * | 3/2017 | Bjaerum | A61B 8/461 |
| 2017/0143313 A1 | 5/2017 | Pelisser et al. | |
| 2019/0336101 A1 * | 11/2019 | Chiang | G01S 7/5202 |

FOREIGN PATENT DOCUMENTS

| | | |
|---|---|---|
| JP | 2005044321 A | 2/2005 |
| KR | 101645377 B1 | 7/2015 |
| WO | WO2014077606 A1 | 5/2014 |
| WO | WO2016183389 A1 | 11/2016 |

OTHER PUBLICATIONS

Philips Lumify Portable Ultrasound Machine, Jul. 10, 2017, https://www.lumify.philips.com/web/.

Clarius Handheld Wireless Ultrasound Scanner, Jul. 10, 2017, https://www.clarius.me/.

Prashanth et al., Image scaling comparison using universal image quality index, In Advances in Computing, Control, & Telecommunication Technologies, 2009, ACT'09, International Conference on (pp. 859-863), IEEE.

Huynh-Thu et al., Scope of validity of PSNR in image/video quality assessment, Electronics Letters, 2008, 44 (13): 800. doi:10.1049/el:20080522.

Z. Wang et al., Image quality assessment: From error visibility to structural similarity, Apr. 2004, vol. 13, No. 4, pp. 600-612.

Gore et al., Full reference image quality metrics for JPEG compressed images. AEU—International Journal of Electronics and Communications, Feb. 1, 2015, 69 (2): 604-608. doi:10.1016/j.aeue.2014.09.002.

Mobisante Inc., Mobisante Ultrasound Imaging, Product Brochure, 2011.

* cited by examiner

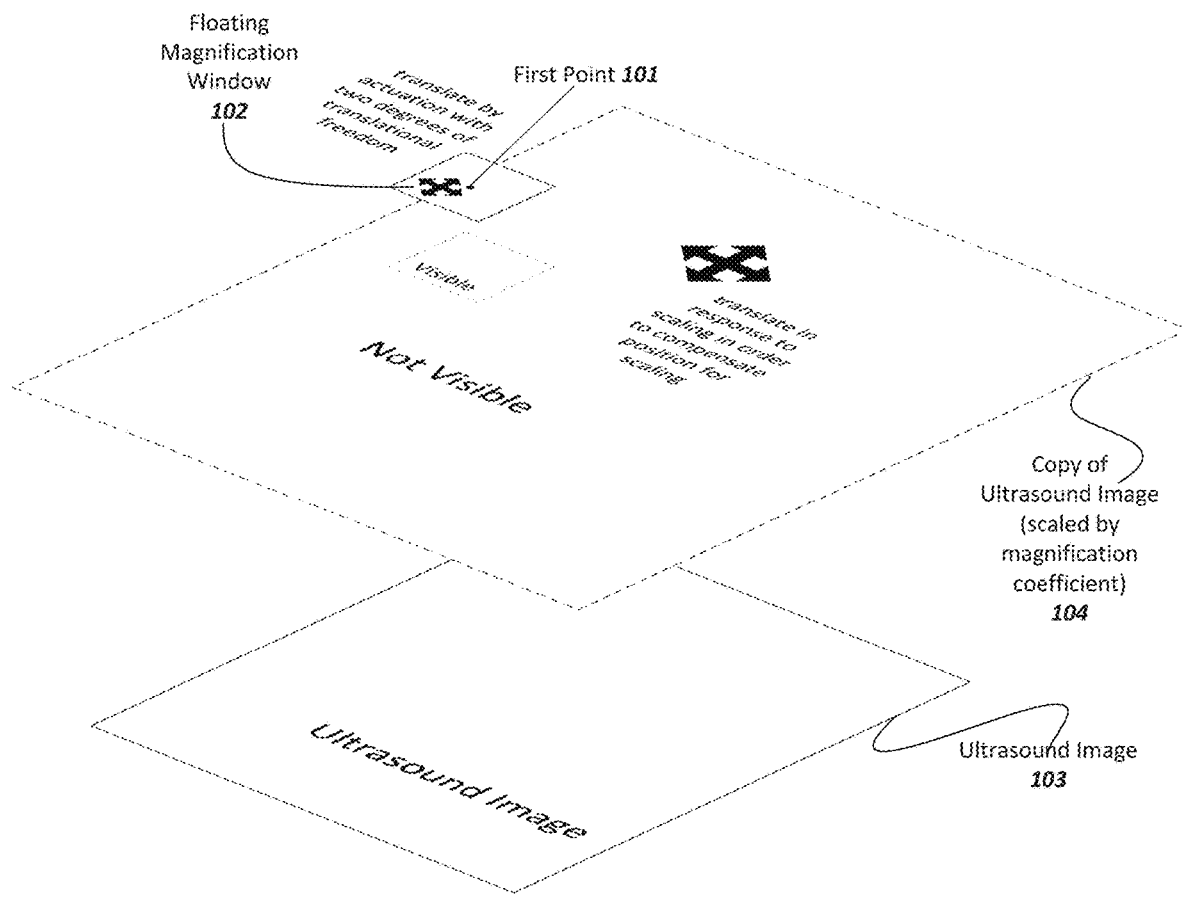
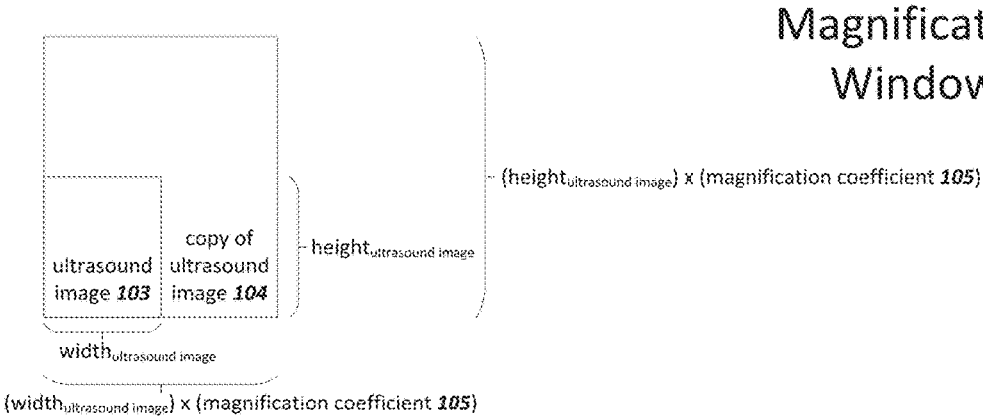
FIG. 1
Floating Magnification Window

How a Reference Gesture Improves Precision

Ellipse
($Swipe_{length} = Ellipse^1_{width}$)

Ellipse
(Swipe$_{length}$ = Width$_\Delta$)**

Ellipse
($Swipe_{length} = X^1$)

Ellipse
(Swipe$_{length}$ = X$_\Delta$)**

TOUCHSCREEN METHOD FOR MEDICALLY PRECISE MEASUREMENTS IN ULTRASOUND IMAGES

CROSS-REFERENCES TO RELATED APPLICATIONS

This non-provisional application claims the benefit of U.S. Provisional Patent Application No. 62/746,775, filed Oct. 17, 2018, the specification of which is incorporated herein in its entirety by reference.

FIELD OF THE CLAIMED INVENTION

The present invention generally relates to medically precise methods of measuring the distance between two points, measuring an angle formed by three points, and positioning an ellipse using the touchscreen of, for example, a mobile device.

BACKGROUND OF THE CLAIMED INVENTION

While the handheld ultrasound market is growing faster than that of larger legacy machine technology, it can be difficult for medical professionals to use mobile devices with smaller screens to view ultrasound images for the purpose of making an accurate diagnosis. To perform a measurement on an ultrasound image, a certain number of points must be marked on the image. The number of points is determined by the type of measurement. To illustrate, a distance measurement requires two points, an angle measurement requires three points, an ellipse requires four points, etc. The precision of these points determines the fidelity of the measurement, which directly impacts the accuracy of the diagnosis. Currently, selecting points on a touch screen has a very low accuracy and does not allow for an ideal selection precision, i.e., within one or two pixels.

For example, in order to actuate a point, the fingertip 201 must push or slide the point. Since this requires a sliding motion of the fingertip 201, this is not effective in situations where the point must only be moved a fraction of a millimeter. A new method of actuating a point is necessary to nudge it with the necessary degree of medical precision.

Also, although a floating magnification window 102 is necessary for medically precise positioning of a point, the medically important area of interest 301 would be partially obscured by the floating magnification window 102 if the techniques known in the art to define and resize an ellipse are used.

SUMMARY OF THE CLAIMED INVENTION

The present invention comprises a medically precise method of measuring the distance between two points on an ultrasound image. The method involves actuation of each point without moving the fingertip 201 by increasing or decreasing contact pressure that causes the 3-dimensional shape of the fingertip 201 to change. The change in the 3-dimensional shape of the fingertip causes a change in the 2-dimensional area of contact with the multi-touch input surface 206. That change in the 2-dimensional area of contact with the multi-touch input surface may be detected through a second plurality of contact points 205 associated with the changed finger contact. This enables the user to actuate the first point 101 and the floating magnification window 102 without moving the fingertip 201 by increasing or reducing contact pressure or by shifting pressure to one side or corner of the fingertip 201. This allows a very slight actuation of the first point 101 (slighter than the actuation achieved by normal methods in the prior art such as pushing or sliding the fingertip), which is conducive to the medical precision necessary for this field of endeavor.

The present invention further comprises a method of measuring an angle formed by three points that have been actuated into position, wherein the second point is the vertex of the angle.

The present invention also comprises a method of generating an ellipse using only two points and a finger swipe gesture 402, whereas ellipses known in the art are scaled via a plurality of actuation points on the ellipse or in a bounding box that surrounds the ellipse. Although the floating magnification window is necessary for medically precise positioning, the medically important area of interest 301 would be partially obscured by the floating magnification window 102 if the techniques known in the art to define and resize an ellipse are used. Instead, by actuating each point of an axis of the ellipse 401 first, the actuation of each point does not obscure the medically important area of interest 301. The ellipse 401 is then generated with poles aligned to according to the axis defined by the two points.

Once the ellipse 401 is generated, the user then scales the width accordingly using a finger swipe gesture 402. However, since the finger swipe gesture 402 does not originate from a point on the ellipse 401, the swipe motion is only used by the ellipse as a reference to scale the width. In contrast, ellipses that are known in the art are scaled by actuation directly on a point on the ellipse or in a bounding box surrounding the ellipse. The advantage of using a reference gesture (as opposed to direct actuation) is that the length of the reference gesture is greater than the change in width. Thus, the width can be scaled proportionately such that larger movements of the swipe only scale the width slightly. This allows greater granularity and, therefore, medically necessary precision. In contrast, scaling by direct actuation of the ellipse would be limited by the position and orientation of the ellipse and micro adjustments to the width would require impractical touch sensitivity.

As would be understood by one of ordinary skilled in the art, a reference to: computer storage media may include cloud storage; measurements can be on a still image or a video loop; a "mask" may be used in accordance with the present invention, but the present invention may be one where a "mask" is not deployed; an "ultrasound" system may include other imaging modalities such as MRI, PET, CT, etc.

The features of the present invention may be applied in non-medical applications, such as photo editing, gaming, etc. Further, the present invention encompasses automatic diagnostic measurements that may be calculated as a result of the present measurement features. Examples may include crown/rump length (straight line measurement), fetal circumference (ellipse), etc.

BRIEF DESCRIPTION OF CLAIMED DRAWINGS

The features and advantages of the present invention will become apparent from a consideration of the following detailed description presented in connection with the accompanying drawings in which:

FIG. 1 is a diagram showing the layers involved in generating the floating magnification window 102. Since the only area of the copy 104 of the ultrasound image 103 that is visible is the area enclosed by the square frame of the floating magnification window 102, the ultrasound image 103 remains visible as the floating magnification window 102 traverses the multi-touch input surface 206. FIG. 1 also shows that the copy 104 of the ultrasound image 103 is a magnification of the ultrasound image 103, produced by multiplying the height and width each by the magnification coefficient 105.

FIG. 2 is a diagram showing a gesture that actuates a point without moving the fingertip 201. The gesture involves changing the pressure at the fingertip 201 such that the 3-dimensional shape of the fingertip 201 changes. The change of the 3-dimensional shape causes the contact points 204 on the multi-touch input surface 206 to change to a new set of contact points 205, even though the fingertip has not moved. The shape of the mask surrounding the first plurality of contact points 204 is compared to the shape of the mask surrounding the second plurality of contact points 204 to determine an imminent motion of the fingertip 201. An "imminent motion" is used herein to emphasize that the fingertip 201 does not move, distinguishing the actuation method of the present invention with the methods of moving a point that are known in the art. Actuation of a point enables a nudge movement such that the user can move the point by shifting the pressure to a side or corner of the finger without moving the finger. Shifting the pressure to a side causes a redistribution of contact points to that area. This technique allows the very slightest movement of the point, which is necessary for medical precision. Due to a pressure change at the fingertip, the concentration of contact points changes, which changes the shape of the mask. The direction of an imminent gesture is indicated by comparing the first mask and the second mask.

Figure 3:
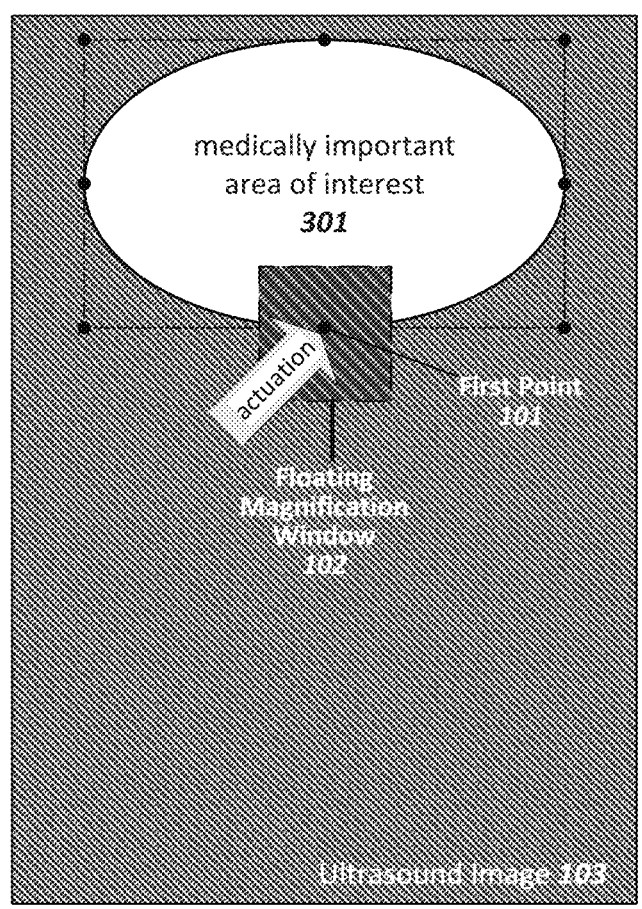

FIG. 3 is a layout showing the spatial relationships between screen elements that include a point that's responsive (in two dimensions of translational freedom) to actuation by a human user, a floating magnification window 102 configured to display a magnification of the underlying ultrasound image 103 within the perimeter of the window and further configured to match the translation of the point, and a medically important area of interest 301 bounded by a scalable and movable ellipse 401. The ellipse 401 is scalable according to methods known in the art, such as (for example) a concentric bounding box with eight actuation points. The ellipse 401 is scaled by actuating any of the actuation points. The floating magnification window is necessary for medically precise positioning. However, using techniques known in the art to define/resize an ellipse, the medically important area of interest would be partially obscured by the floating magnification window.

Figure 4:
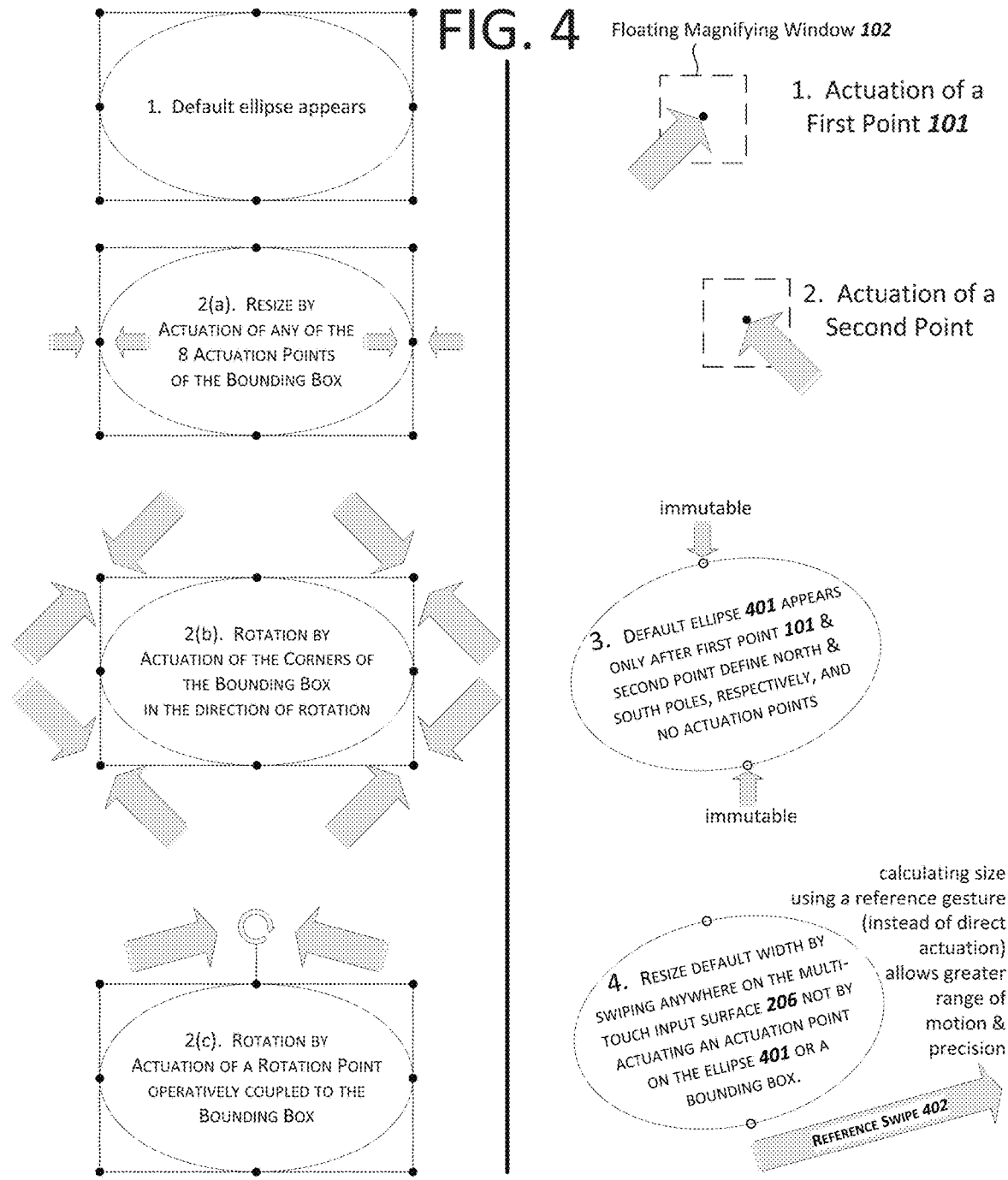

FIG. 4 distinguishes the method of the present invention from the method (known in the art) of scaling and rotating an ellipse 401.

Figure 5:
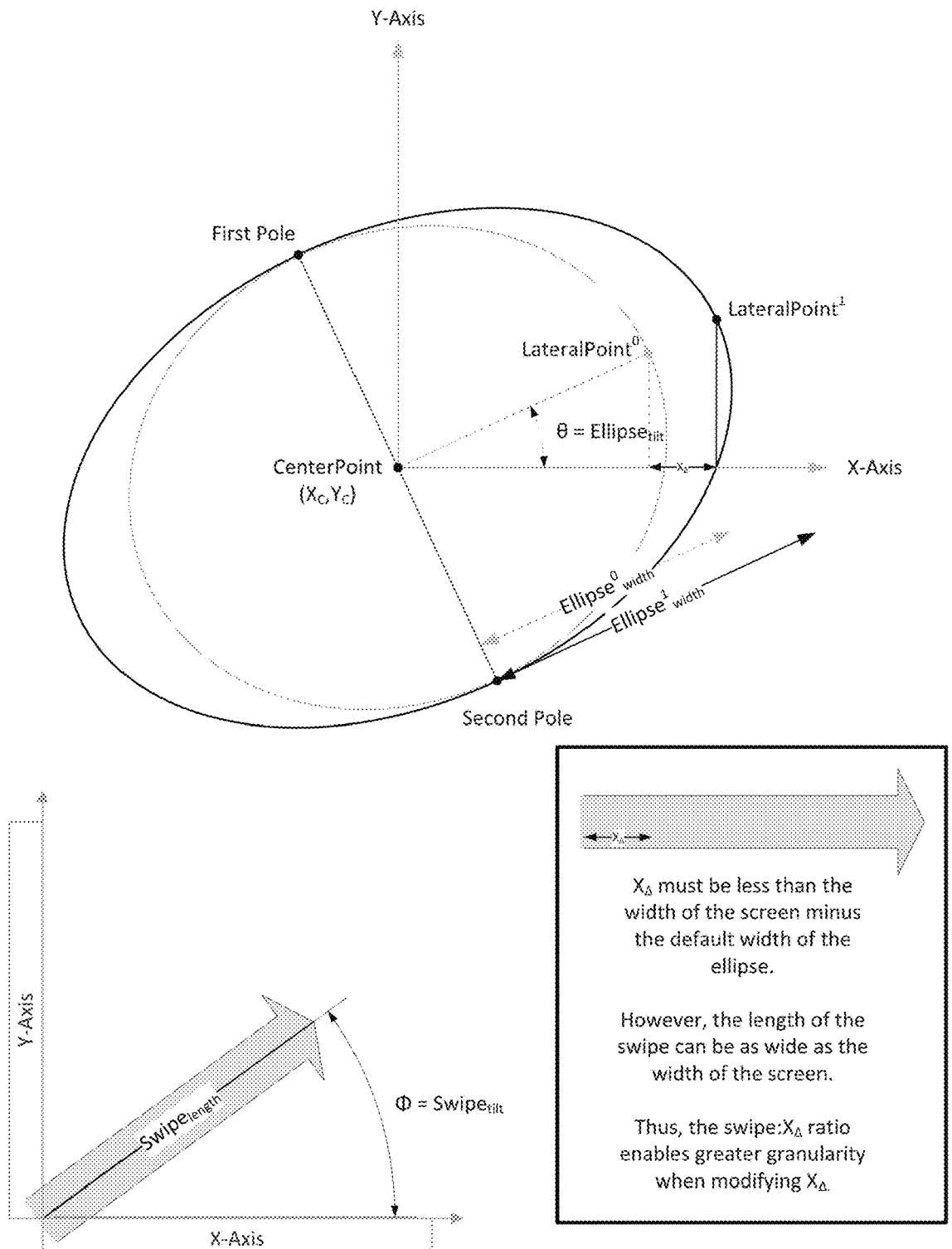

FIG. 5 illustrates the advantage of modifying the width of an ellipse 401 using a reference gesture instead of using direct actuation of an actuation point. The inset of FIG. 3 shows that the change in the width of an ellipse 401 (represented by ΔX) is less than the length of the finger swipe gesture 402, and that this proportion enables the finger swipe gesture 402 to adjust the width with greater granularity/precision.

Figure 6:
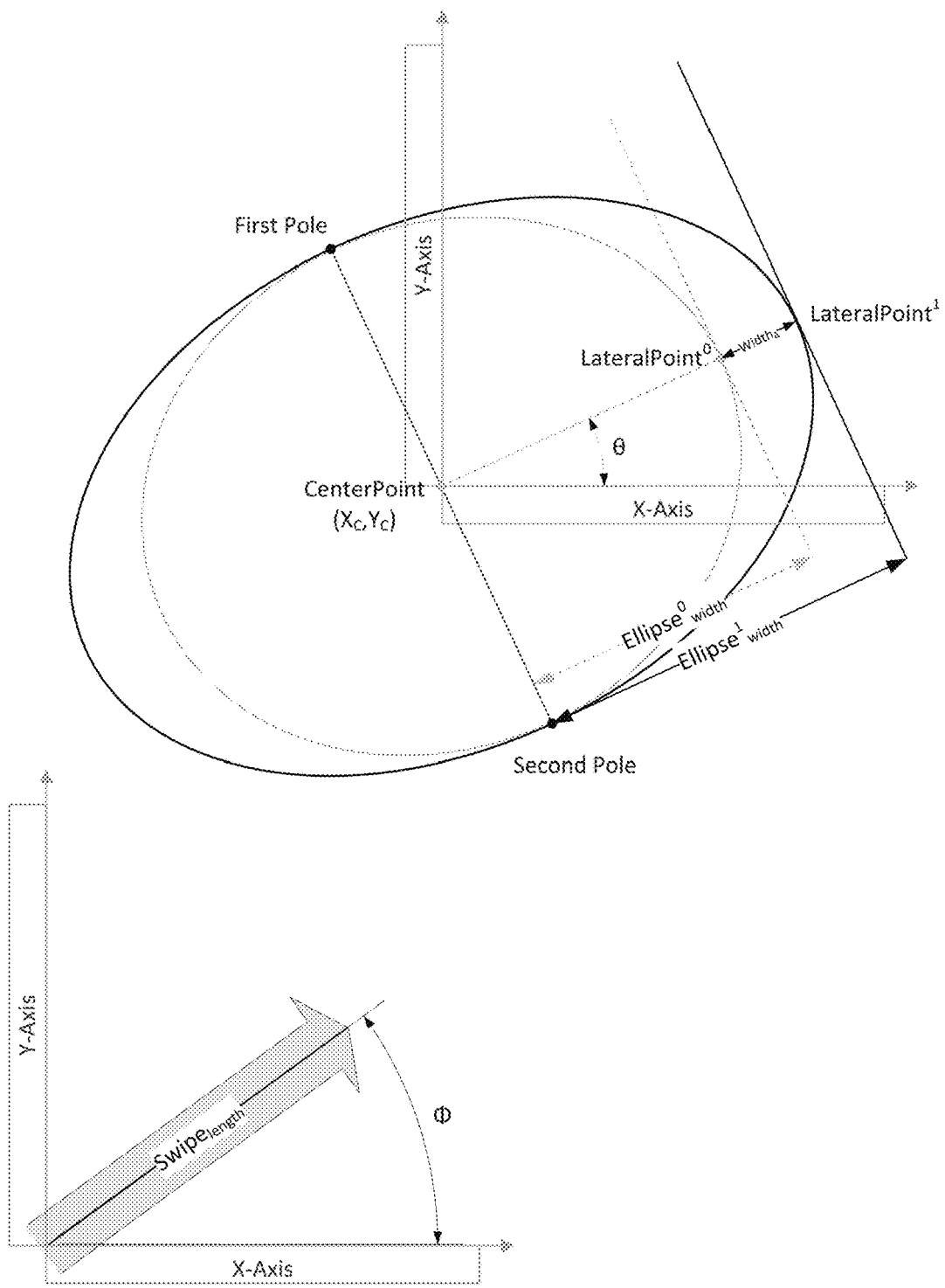

FIG. 6 is an exemplary calculation of the finger swipe gesture 402 such that the length of the finger swipe gesture 402 sets the width of the ellipse 401.

Figure 7:
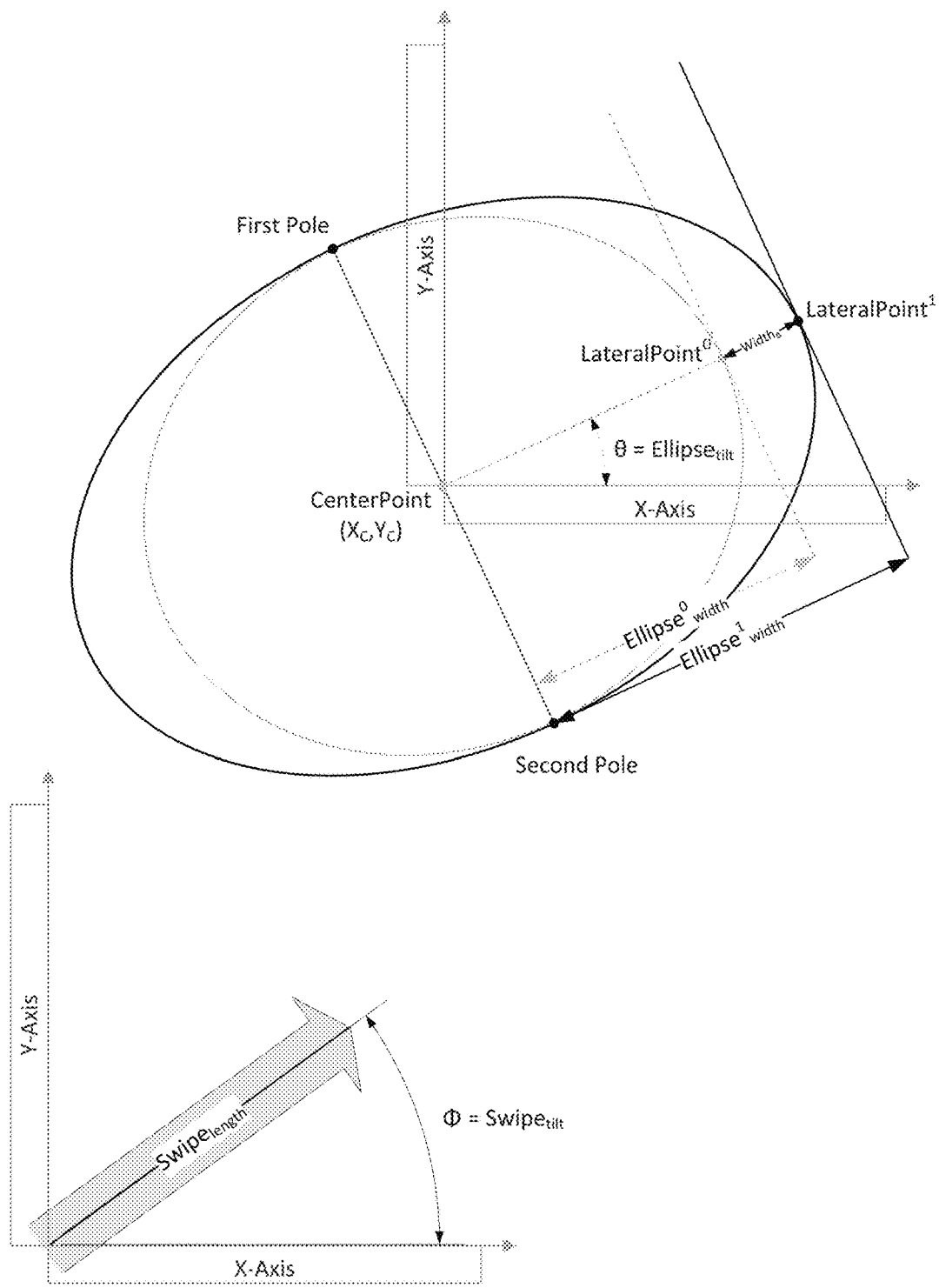

FIG. 7 is an exemplary calculation of the finger swipe gesture 402 such that the length of the finger swipe gesture 402 is added to the width of the ellipse 401.

Figure 8:
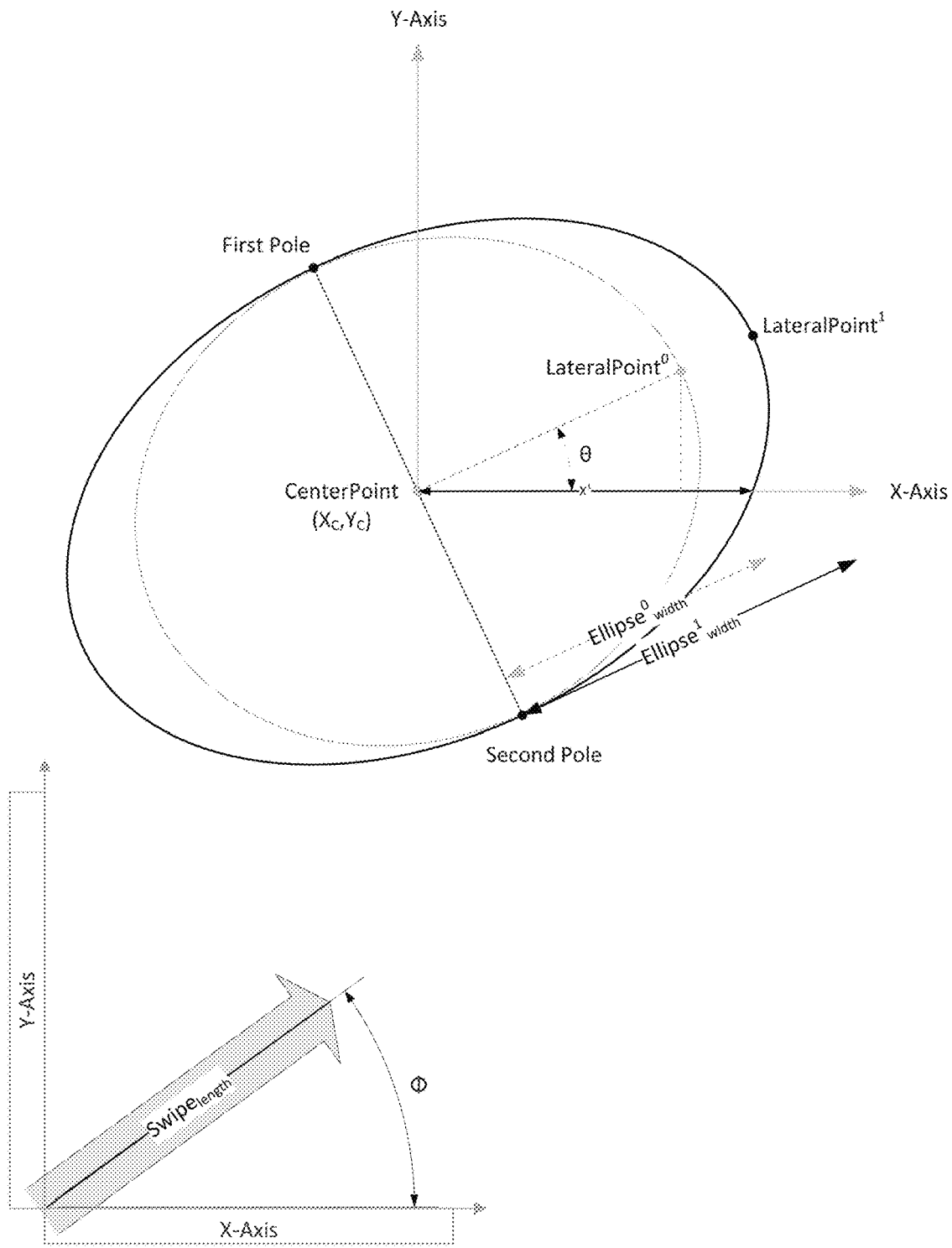

FIG. 8 shows an exemplary calculation of the finger swipe gesture 402 such that the length of the finger swipe gesture 402 determines the X coordinate of a LateralPoint on the ellipse 401.

Figure 9:
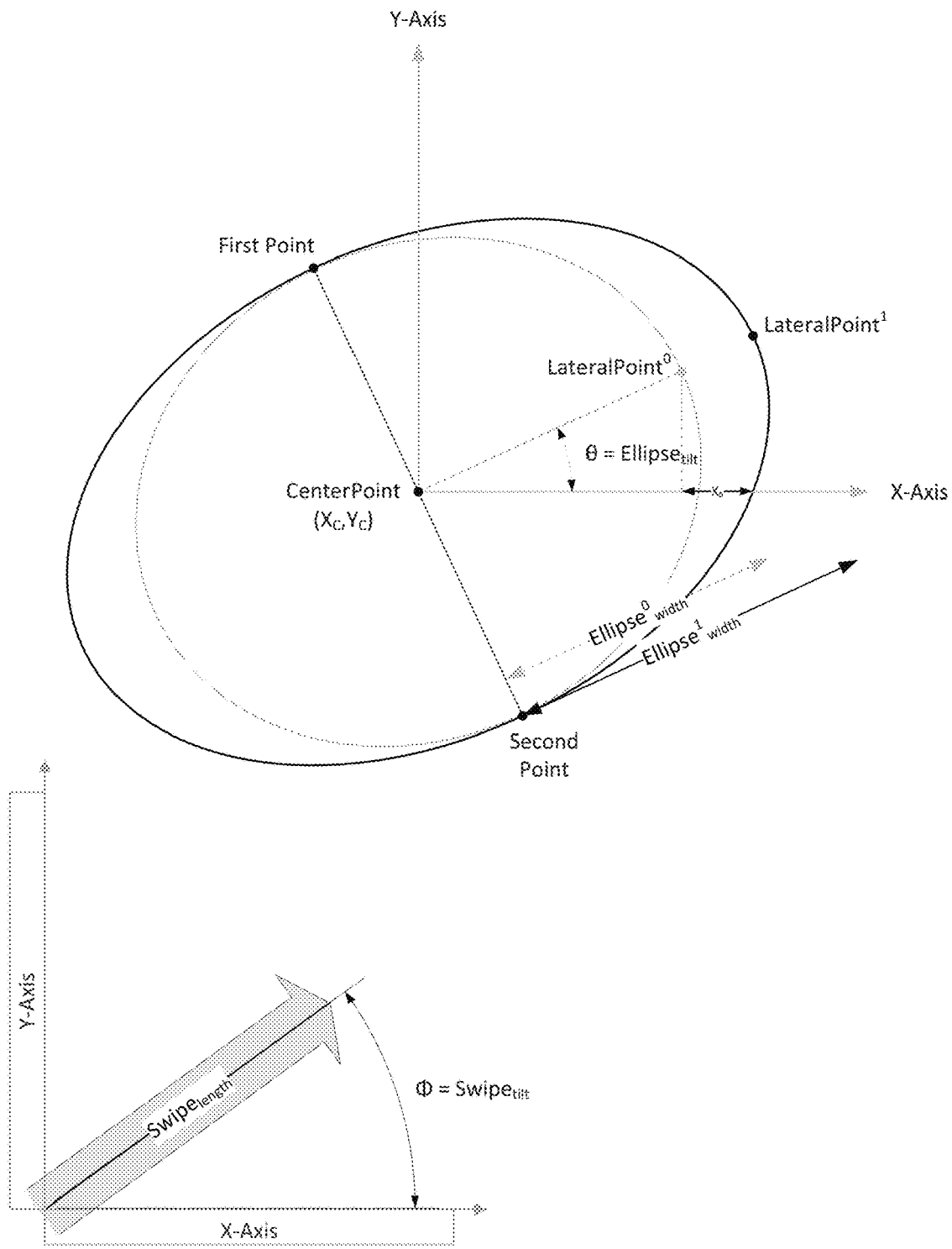

FIG. 9 shows an exemplary calculation of the finger swipe gesture 402 such that the length of the finger swipe gesture 402 determines the length that's added to the X coordinate of a LateralPoint on the ellipse 401.

DETAILED DESCRIPTION OF THE PRESENT INVENTION

The following description sets forth numerous specific details (e.g., specific configurations, parameters, examples, etc.) of the disclosed embodiments, examples of which are illustrated in the accompanying drawings. It should be recognized, however, that such description is not intended as a limitation on the scope of the disclosed embodiments, but is intended to elaborate upon the description of these embodiments. It will be evident to a person of ordinary skill in the art that the present invention can be practiced without every specific detail described infra. Moreover, well-known methods, procedures, components, and circuits have not been described in detail so as not to unnecessarily obscure aspects of the embodiments of the present invention.

It is fully contemplated that the features, components, and/or steps described with respect to one embodiment may be combined with the features, components, and/or steps described with respect to other embodiments of the present disclosure. To avoid needless descriptive repetition, one or more components or actions described in accordance with one exemplary embodiment can be used or omitted as applicable from other embodiments. For the sake of brevity, the numerous iterations of these combinations will not be described separately. The same reference numbers may be used to refer to the same or similar elements in different drawings. Alternately, different reference numbers may be used to refer to the same or similar elements in the drawings of different embodiments. Any distinction of an element's reference number in one embodiment from another is not limiting in any way, does not suggest that elements of one embodiment could not be combined with or substituted for elements in another embodiment, and (most importantly) is specifically intended only to facilitate the matching of elements in the disclosure to their corresponding claim recitations.

Embodiments within the scope of the present invention may comprise non-transitory computer-readable media for storing computer-executable instructions. Instructions that cause at least one processing circuit to perform one or more operations are "computer-executable." The term "non-transitory" is used herein to distinguish two distinctly different kinds of computer-readable media: physical storage media that stores computer-executable instructions and transmission media that carries computer-executable instructions. Physical storage media includes RAM and other volatile types of memory; ROM, EEPROM and other non-volatile types of memory; CD-ROM, CD-RW, DVD-ROM, DVD-RW and other optical disk storage; magnetic disk storage or other magnetic storage devices; and any other tangible medium that can store computer-executable instructions that can be accessed and processed by at least one processing circuit.

Transmission media can include signals carrying computer-executable instructions over a network to be received by a general-purpose or special-purpose computer. Embodiments of the present invention expressly (by exemplary recitation such as "non-transitory") exclude signals carrying computer-executable instructions. However, it should be understood that once a signal carrying computer-executable instructions is received by a computer, the type of computer-readable storage media transforms automatically from transmission media to physical storage media. This transformation may even occur early on in intermediate memory such as (by way of example and not limitation) a buffer in the RAM of a network interface card, regardless of whether the buffer's content is later transferred to less volatile RAM in the computer. Thus, devices that merely repeat a signal are contemplated by the embodiments of the present invention, even though the media that carry the signal between such devices and the signal itself are expressly not included within the claim scope. Thus, it should be understood that "non-transitory computer-readable storage media" is used herein instead of simply "physical storage media" or "physical computer-readable storage media" in order to underscore that even transmission media necessarily involves eventual transformation into physical storage media and to therefore capture all embodiments where the computer-readable instructions are stored in physical storage media—even if only temporarily before transforming back into transmission media.

Those skilled in the art will appreciate that the present invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, and the like. The present invention may also be practiced in distributed system environments where operations are delegated to and/or shared between local and remote computer systems across a network. In a distributed system environment, program modules may be located in both local and remote memory storage devices. "Multi-touch input surface" includes capacitive and resistive surfaces.

Where two or more elements are said to be "coupled," the meaning shall include (in addition to configurations where the elements directly operate with each other because they are joined) configurations where the elements indirectly operate with each other (e.g., through one or more intermediate elements) so long as there is a link.

It will be appreciated that the terms "superior" and "inferior" are used as known in the art to mean "above" and "below," respectively. When the term "lateral" is used to describe a position relative to a center, the most lateral element is the element furthest away from the center. However, as used herein, these terms identify elements rather than describe the most recent state of their orientation and position. Thus, translation, rotation, reflection, and mirroring do not cause a reassessment or relabeling of the described elements. For example, where a superior point is defined as the point "superior to all other points of the ellipse," the present invention tracks that same point by this label throughout the claims regardless of whether operations (such as translation, rotation, reflection, and mirroring) cause other points to become superior to the superior point. Restated, the superior point is labeled in terms of its initial state and retains that label throughout the claims. Similarly, elements that are labeled according to their initial position or orientation retain that label throughout the claims regardless of how that position or orientation may change.

When used herein, terms describing direction, position, and orientation (such as, but not limited to, "superior," "interior," "lateral", and "center") are not limiting upon the claims unless expressly recited therein.

In some embodiments, a graphical user interface may be implemented on a computing device, such as (but not limited to) a mobile computing device, wherein the mobile computing device comprises a processor for executing instructions, RAM, a multi-touch input surface, an I/O interface configured to connect a handheld ultrasound device as a peripheral device, and hard disk memory upon which are stored computer-executable instructions for the graphical user interface. The graphical user interface may comprise a distance-measuring module, an angle-measuring module, and an ellipse-generating module.

In some embodiments, when executed by the processor of the computing device, the instructions constituting the distance-measuring module may cause the processor to perform operations. The operations may comprise displaying a first point 101 on an ultrasound image 103 and a floating magnification window 102. In some embodiments, the floating magnification window 102 may be a square frame that is concentric to the first point 101, configured to display an area of magnification by cropping a magnified copy 104 of the ultrasound image 103.

In some embodiments, the height and width of the copy 104 of the ultrasound image 103 may be scaled by a magnification coefficient 105. In some embodiments, the copy 104 of the ultrasound image 103 may be translated to compensate for the scaling and maintain a position of the copy 104 of the ultrasound image 103 relative to the square frame. In some embodiments, the translation may be based on, for example, a fraction of the difference between the size of the ultrasound image 103 and its copy 104.

In some embodiments, the first point may be configured to translate with two dimensions of translational freedom upon actuation by a user. In some embodiments, the floating magnification window 102 may be configured to match the translation of the first point 101 caused when a user actuates the first point 101.

In some embodiments, the size of the floating magnification window may be automatically reduced (by considering the width and height of the multi-touch input surface 206) when the location of the first point 101 is near the perimeter of the multi-touch input surface 206, such that there is not enough space to fully display the floating magnification window 102.

In some embodiments, actuation may involve detecting a first plurality of contact points 204 associated with the contact of a fingertip 201 on the multi-touch input surface 206. In some embodiments, the contact points 204 may be encompassed by a first mask 202, wherein the first mask 202 is a closed shape. In some embodiments, the calculation of the first mask 202 is performed in the background without displaying the first mask 202.

Even though the fingertip 201 has not moved, the contact of the fingertip 201 may change because of, for example, increased or decreased contact pressure that causes the 3-dimensional shape of the fingertip 201 to change. The change in the 3-dimensional shape of the fingertip may cause a change in the 2-dimensional area of contact with the multi-touch input surface 206. In some embodiments, that change in the 2-dimensional area of contact with the multi-touch input surface may be detected through a second plurality of contact points 205 associated with the changed finger contact. This enables the user to actuate the first point 101 and the floating magnification window 102 without moving the fingertip 201 by increasing or reducing contact pressure or by shifting pressure to one side or corner of the fingertip 201. This allows a very slight actuation of the first point 101 (slighter than the actuation achieved by normal methods in the prior art such as pushing or sliding the fingertip), which is conducive to the medical precision necessary for this field of endeavor.

In some embodiments, the contact points 205 may be encompassed by a second mask 203, wherein the second mask 203 is a closed shape. In some embodiments, the calculation of the second mask 203 is performed in the background without displaying the second mask 203.

In some embodiments, the anticipated direction of the user's fingertip 201 may be determined by comparing the second mask 203 to the first mask 202. In some embodiments, the first point 101 and the floating magnification window 102 may be translated based on the anticipated direction of the imminent motion of the fingertip 201. The "imminent motion" described herein is distinguished from actual motions where the fingertip slides, such as typical motions known in the prior art.

In some embodiments, the user may actuate the first point 101 to a first destination, wherein actuating is a gesture with continuous contact with the multi-touch input surface 206. In some embodiments, when the user disengages the first point 101, the floating magnification window 102 may disappear.

In some embodiments, a second point may be displayed on the ultrasound image 103 with configurations and functionality that are the same as those of the first point 101. In some embodiments the floating magnification window 102 may be displayed with the same functionality as before but with configurations directed to the second point rather than the first point 101.

In some embodiments, the user may actuate the second point to a second destination, wherein actuating is a gesture with continuous contact with the multi-touch input surface 206. In some embodiments, when the user disengages the second point 101, the floating magnification window 102 may disappear.

In some embodiments, a distance between the first point 101 and the second point may be calculated.

In some embodiments, when executed by the processor of the computing device, the instructions constituting the angle-measuring module may cause the processor to perform operations. The operations may comprise displaying a first point 101 on the ultrasound image 103 with the same configurations and functionality as above. In some embodiments, the floating magnification window 102 may be displayed with the same functionality and configurations directed to the first point 101. In some embodiments, the first point 101 and the floating magnification window 102 may be actuated to a first destination, whereupon the floating magnification window 102 may disappear. In some embodiments, a second point may be displayed on the ultrasound image 103 with the same configurations and functionality as above. In some embodiments, the floating magnification window 102 may be displayed with the same functionality and configurations directed to the second point. In some embodiments, the second point and the floating magnification window 102 may be actuated to a second destination, whereupon the floating magnification window 102 may disappear.

In some embodiments, a third point may be displayed on the ultrasound image 103 with configurations and functionality that are the same as those of the first point 101. In some embodiments the floating magnification window 102 may be displayed with the same functionality as before but with configurations directed to the third point rather than the first point 101.

In some embodiments, the user may actuate the third point to a third destination, wherein actuating is a gesture with continuous contact with the multi-touch input surface 206. In some embodiments, when the user disengages the third point 101, the floating magnification window 102 may disappear.

In some embodiments, an angle (formed by the first point 101, the second point as its vertex, and the third point) may be measured.

In some embodiments, when executed by the processor of the computing device, the instructions constituting the ellipse-generating module may cause the processor to perform operations. The operations may comprise displaying a first point 101 on the ultrasound image 103 with the same configurations and functionality as above. In some embodiments, the floating magnification window 102 may be displayed with the same functionality and configurations directed to the first point 101. In some embodiments, the first point 101 and the floating magnification window 102 may be actuated to a first destination, whereupon the floating magnification window 102 may disappear. In some embodiments, a second point may be displayed on the ultrasound image 103 with the same configurations and functionality as above. In some embodiments, the floating magnification window 102 may be displayed with the same functionality and configurations directed to the second point. In some embodiments, the second point and the floating magnification window 102 may be actuated to a second destination, whereupon the floating magnification window 102 may disappear.

In some embodiments, an ellipse 401 may be displayed on the ultrasound image 103. In some embodiments, the ellipse 401 may comprise a superior point, an inferior point, and a lateral point, wherein the superior point, the inferior point, and the lateral point are points on the ellipse, wherein the superior point is superior to all other points of the ellipse 401, the inferior point is inferior to all other points of the ellipse 401, and the lateral point is a maximum lateral distance from center of the ellipse 401. In some embodiments, the height of the ellipse 401 is scaled to match the distance between the first point 101 and the second point. In some embodiments, the ellipse 401 is rotated to align the superior point to the first point 101 at the first destination and the inferior point to the second point at the second destination.

In some embodiments, the ellipse 401 is configured to be unresponsive to actuation by direct touch. In some embodiments, the width of the ellipse 401 can be scaled by a finger swipe gesture 402 only if the finger swipe gesture 402 does not originate from a point on the ellipse 401.

Thus, in contrast to scalable ellipses that are known in the art, the ellipse 401 of the present invention is defined and scaled by two points and a finger swipe gesture 402, whereas ellipses known in the art are scaled via a plurality of actuation points on the ellipse or in a bounding box that surrounds the ellipse. FIG. 3 shows that, although the floating magnification window is necessary for medically precise positioning, the medically important area of interest 301 would be partially obscured by the floating magnification window 102 if the techniques known in the art to define and resize an ellipse are used. FIG. 4 further compares the known methods with the method of the present invention. By actuating each point of an axis of the ellipse 401 first, the actuation of each point does not obscure the medically important area of interest 301.

Once the ellipse 401 is generated, the user then scales the width accordingly using a finger swipe gesture 402. However, since the finger swipe gesture 402 does not originate from a point on the ellipse 401, the swipe motion is only used by the ellipse as a reference to scale the width. In contrast, ellipses that are known in the art are scaled by actuation directly on a point on the ellipse or in a bounding box surrounding the ellipse. FIG. 5 shows an exemplary advantage of using a reference gesture (as opposed to direct actuation) is that the length of the reference gesture is greater than the change in width. Thus, the width can be scaled proportionately such that larger movements of the swipe only scale the width slightly. This allows greater granularity and, therefore, medically necessary precision. In contrast, scaling by direct actuation of the ellipse would be limited by the position and orientation of the ellipse and micro adjustments to the width would require impractical touch sensitivity.

In some embodiments, the finger swipe gesture 402 may be detected and, responsive to the finger swipe gesture 402, the width of the ellipse 401 may be scaled based on one or more attributes of the finger swipe gesture 402. In some embodiments, the ellipse 401 is configured to be immutable once the width of the ellipse 401 has been scaled by the finger swipe gesture 402. In contrast, ellipses that are known in the art are always scalable.

The computing devices may include desktop computers, laptops, tablets, e-readers, personal digital assistants, smartphones, gaming devices, servers, and computer systems such as massively parallel systems. The computing devices may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., CD-RW, CD-ROM, DVD-RW, DVD-ROM, flash memory, etc.) and include other storage means. The computer-readable storage media may have recorded upon or may be encoded with computer-executable instructions that cause at least one processing circuit to perform operations. The data transmission media is used for transmitting data via transitory, propagating signals or carrier waves (e.g., electromagnetism) via a wired or wireless connection.

While illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

In some embodiments, the figures presented in this patent application are drawn to scale, including the angles, ratios of dimensions, etc. In other embodiments, the figures are representative only and the claims are not limited by the dimensions of the figures.

The invention claimed is:

1. A method for taking medically precise measurements with a multi-touch input surface 206, the method comprising:
   A. displaying, by a graphical user interface:
      i. a first point 101 on an ultrasound image 103, wherein the first point 101 is configured to translate with two dimensions of translational freedom upon actuation by a user, and
      ii. a floating magnification window 102, wherein displaying the floating magnification window 102 comprises calculating a square frame based on the first point 101, a size of an area of magnification, a width of the multi-touch input surface 206, and a height of the multi-touch input surface 206, wherein the square frame is configured to crop a copy 104 of the ultrasound image 103, wherein the floating magnification window 102 is concentric with the first point 101 and configured to:
         a. match the translation of the first point 101, and
         b. display a magnification of a region of the ultrasound image 103 that is bounded by the floating magnification window 102, wherein displaying the magnification comprises:
            I. scaling by a magnification coefficient 105 a height and a width of the copy 104 of the ultrasound image 103, and
            II. translating the copy 104 of the ultrasound image 103 based on the magnification coefficient 105 to compensate for the scaling and maintain a position of the copy 104 of the ultrasound image 103 relative to the square frame;
   B. actuating, by the user, the first point 101 to a first destination, wherein actuating is a gesture with continuous contact with the multi-touch input surface 206, wherein the floating magnification window 102 disappears when the user disengages the first point 101, wherein actuating comprises:
      i. detecting, by the multi-touch input surface 206, a first plurality of contact points 204 associated with a finger contact of a fingertip 201,
      ii. calculating, by the graphical user interface, a first mask 202 for the first plurality of contact points 204 associated with the finger contact, wherein the first mask 202 is a closed shape, wherein the calculating is performed in the background without displaying the first mask 202,
      iii. detecting, by the multi-touch input surface 206, a second plurality of contact points 205 associated with the finger contact, wherein the second plurality of contact points 205 is caused by a change in a 3-dimensional shape of the fingertip 201, wherein the change in the 3-dimensional shape of the fingertip 201 is caused by a redistribution of touch pressure associated with an imminent motion of the fingertip 201,
      iv. calculating by the graphical user interface, a second mask 203 for the second plurality of contact points 205 associated with the finger contact, wherein the second mask 203 is a closed shape, wherein calculating is performed in the background without displaying the second mask 203,
      v. determining, by the graphical user interface, an anticipated direction of the imminent motion of the fingertip 201 by comparing the second mask 203 to the first mask 202, and vi. translating, by the graphical user interface, the first point 101 and the floating magnification window 102 based on the anticipated direction of the imminent motion of the fingertip 201;

C. displaying, by the graphical user interface:
   i. a second point on the ultrasound image 103, wherein the second point is configured to translate with two dimensions of translational freedom upon actuation by the user, and
   ii. the floating magnification window 102, wherein the floating magnification window 102 is concentric with the second point and configured to:
      a. match the translation of the second point, and
      b. display the magnification of the region of the ultrasound image 103 that is bounded by the floating magnification window 102;
         I. scaling by the magnification coefficient 105 the height and the width of the copy 104 of the ultrasound image 103, and
         II. translating the copy 104 of the ultrasound image 103 based on the magnification coefficient 105 to compensate for the scaling and maintain the position of the copy 104 of the ultrasound image 103 relative to the square frame;

D. actuating, by the user, the second point to a second destination, wherein actuating is a gesture with continuous contact with the multi-touch input surface 206, wherein the floating magnification window 102 disappears when the user disengages the second point, wherein actuating comprises:
   i. detecting, by the multi-touch input surface 206, the first plurality of contact points 204 associated with the finger contact of the fingertip 201,
   ii. calculating, by the graphical user interface, the first mask 202 for the first plurality of contact points 204 associated with the finger contact, wherein the first mask 202 is the closed shape, wherein the calculating is performed in the background without displaying the first mask 202,
   iii. detecting, by the multi-touch input surface 206, the second plurality of contact points 205 associated with the finger contact, wherein the second plurality of contact points 205 is caused by the change in the 3-dimensional shape of the fingertip 201, wherein the change in the 3-dimensional shape of the fingertip 201 is caused by the redistribution of touch pressure associated with an imminent motion of the fingertip 201,
   iv. calculating by the graphical user interface, the second mask 203 for the second plurality of contact points 205 associated with the finger contact, wherein the second mask 203 is the closed shape, wherein calculating is performed in the background without displaying the second mask 203,
   v. determining, by the graphical user interface, an anticipated direction of the imminent motion of the fingertip 201 by comparing the second mask 203 to the first mask 202, and
   vi. translating, by the graphical user interface, the second point and the floating magnification window 102 based on the anticipated direction of the imminent motion of the fingertip 201; and E. calculating, by the graphical user interface, a distance between the first point 101 and the second point.

2. The method of claim 1, further comprising:
A. displaying, by the graphical user interface:
   i. a third point on the ultrasound image 103, her the third point is configured to translate with two dimensions of translational freedom upon actuation by the user, and
   ii. the floating magnification window 102, wherein the floating magnification window 102 is concentric with the third point and configured to:
      a. match the translation of the third point, and
      b. display the magnification of the region of the ultrasound image 103 that is bounded by the floating magnification window 102, wherein displaying the magnification comprises:
         I. scaling by the magnification coefficient 105 the height and the width of the copy 104 of the ultrasound image 103, and
         II. translating the copy 104 of the ultrasound image 103 based on the magnification coefficient 105 to compensate for the scaling and maintain the position of the copy 104 of the ultrasound image 103 relative to the square frame;

B. actuating, by the user, the third point to a third destination, wherein actuating is a gesture with continuous contact with the multi-touch input surface 206, wherein the floating magnification window 102 disappears when the user disengages the third point, wherein actuating comprises:
   i. detecting, by the multi-touch input surface 206, the first plurality of contact points 204 associated with the finger contact of the fingertip 201,
   ii. calculating, by the graphical user interface, the first mask 202 for the first plurality of contact points 204 associated with the finger contact, wherein the first mask 202 is the closed shape, wherein the calculating is performed in the background without displaying the first mask 202,
   iii. detecting, by the multi-touch input surface 206, the second plurality of contact points 205 associated with the finger contact, wherein the second plurality of contact points 205 is caused by the change in the 3-dimensional shape of the fingertip 201, wherein the change in the 3-dimensional shape of the fingertip 201 is caused by the redistribution of touch pressure associated with an imminent motion of the fingertip 201,
   iv. calculating, by the graphical user interface, the second mask 203 for the second plurality of contact points 205 associated with the finger contact, wherein the second mask 203 is the closed shape, wherein calculating is performed in the background without displaying the second mask 203,
   v. determining, by the graphical user interface, an anticipated direction of the imminent motion of the fingertip 201 by comparing the second mask 203 to the first mask 202, and
   vi. translating, by the graphical user interface, the third point and the floating magnification window 102 based on the anticipated direction of the imminent motion of the fingertip 201; and C. calculating, by the graphical user interface, an angle formed by the first point 101, the second point, and the third point, wherein a vertex of the angle is the second point.

3. The method of claim 1, further comprising:
A. displaying, by the graphical user interface, an ellipse 401 on the ultrasound image 103,
   i. comprising a superior point, an inferior point, and a lateral point, wherein the superior point, the inferior point, and the lateral point are points on the ellipse, wherein the superior point is superior to all other points of the ellipse 401, the inferior point is inferior to all other points of the ellipse 401, and the lateral point is a maximum lateral distance from center of the ellipse 401,
   ii. wherein every point on the ellipse 401 is configured to be unresponsive to actuation by direct touch,
   iii. wherein a width of the ellipse 401 is configured to be scaled by a finger swipe gesture 402 only if an origin point of the finger swipe gesture 402 is not a point on the ellipse 401,
   iv. wherein the ellipse 401 is configured to be immutable after the width of the ellipse 401 has been scaled by the finger swipe gesture 402, and
   v. wherein displaying the ellipse 401 on the ultrasound image 103 comprises:
      a. scaling a height of the ellipse 401 to match the distance between the first point 101 and the second point, and
      b. rotating the scaled ellipse 401 to align the superior point to the first point 101 at the first destination and the inferior point to the second point at the second destination;
B. detecting, by the graphical user interface, the finger swipe gesture 402; and
C. scaling, by the graphical user interface, the width of the ellipse 401 based on one or more attributes of the finger swipe gesture 402.

4. The method of claim 3, wherein scaling the width based on one or more attributes comprises:
A. defining the width of the ellipse as a proportion of a length of the swipe, wherein the proportion is less than or equal to one.

5. The method of claim 3, wherein scaling the width based on one or more attributes comprises:
A. defining the width of the ellipse as a sum of the width of the ellipse and a proportion of a length of the swipe, wherein the proportion is less than or equal to one.

6. The method of claim 3, wherein scaling the width based on one or more attributes comprises:
A. equating an x-coordinate of the lateral point to an x-coordinate of an end point of the finger swipe gesture 402.

7. The method of claim 3, wherein scaling the width based on one or more attributes comprises:
A. equating a y-coordinate of the lateral point to a y-coordinate of an end point of the finger swipe gesture 402.

8. The method of claim 3, wherein scaling the width based on one or more attributes comprises:
A. adding to an x-coordinate of the lateral point a difference between an x-coordinate of an end point of the finger swipe gesture 402 and an x-coordinate of the origin point.

9. The method of claim 3, wherein scaling the width based on one or more attributes comprises:
A. adding to a y-coordinate of the lateral point a difference between a y-coordinate of an end point of the finger swipe gesture 402 and a y-coordinate of the origin point.

10. A non-transitory computer-readable storage medium having computer-executable instructions recorded thereon for taking medically precise measurements with a multi-touch input surface 206 that, when executed by at least one processing circuit, perform a computer process, the computer process comprising:
A. displaying, by the graphical user interface:
   i. a first point 101 on an ultrasound image 103, wherein the first point 101 is configured to translate with two dimensions of translational freedom upon actuation by a user, and
   ii. a floating magnification window 102, wherein displaying the floating magnification window 102 comprises calculating a square frame based on the first point 101, a size of an area of magnification, a width of the multi-touch input surface 206, and a height of the multi-touch input surface 206, wherein the square frame is configured to crop a copy 104 of the ultrasound image 103, wherein the floating magnification window 102 is concentric with the first point 101 and configured to:
      a. match the translation of the first point 101, and
      b. display a magnification of a region of the ultrasound image 103 that is bounded by the floating magnification window 102, wherein displaying the magnification comprises:
         I. scaling by a magnification coefficient 105 a height and a width of the copy 104 of the ultrasound image 103, and
         II. translating the copy 104 of the ultrasound image 103 based on the magnification coefficient 105 to compensate for the scaling and maintain a position of the copy 104 of the ultrasound image 103 relative to the square frame;
B. actuating, by the user, the first point 101 to a first destination, wherein actuating is a gesture with continuous contact with the multi-touch input surface 206, wherein the floating magnification window 102 disappears when the user disengages the first point 101, wherein actuating comprises:
   i. detecting, by the multi-touch input surface 206, a first plurality of contact points 204 associated with a finger contact of a fingertip 201,
   ii. calculating, by the graphical user interface, a first mask 202 for the first plurality of contact points 204 associated with the finger contact, wherein the first mask 202 is a closed shape, wherein the calculating is performed in the background without displaying the first mask 202,
   iii. detecting, by the multi-touch input surface 206, a second plurality of contact points 205 associated with the finger contact, wherein the second plurality of contact points 205 is caused by a change in a 3-dimensional shape of the fingertip 201, wherein the change in the 3-dimensional shape of the fingertip 201 is caused by a redistribution of touch pressure associated with an imminent motion of the fingertip 201,
   iv. calculating, by the graphical user interface, a second mask 203 for the second plurality of contact points 205 associated with the finger contact, wherein the second mask 203 is a closed shape, wherein calculating is performed in the background without displaying the second mask 203, v. determining, by the graphical user interface, an anticipated direction of the imminent motion of the fingertip 201 by comparing the second mask 203 to the first mask 202, and vi. translating, by the graphical user interface, the first point 101 and the floating magnification window 102 based on the anticipated direction of the imminent motion of the fingertip 201:

C. displaying, by the graphical user interface:

i. a second point on the ultrasound image 103, wherein the second point is configured to translate with two dimensions of translational freedom upon actuation by the user, and ii. the floating magnification window 102, wherein the floating magnification window 102 is concentric with the second point and configured to:

a. match the translation of the second point, and b. display the magnification of the region of the ultrasound age 103 that is bounded by the floating magnification window 102, wherein displaying the magnification comprises:

I. scaling by the magnification coefficient 105 the height and the width of the copy 104 of the ultrasound image 103, and II. translating the copy 104 of the ultrasound image 103 based on the magnification coefficient 105 to compensate for the scaling and maintain the position of the copy 104 of the ultrasound image 103 relative to the square frame;

D. actuating, by the user, the second point to a second destination, wherein actuating is a gesture with continuous contact with the multi-touch input surface 206, wherein the floating magnification window 102 disappears when the user disengages the second point, wherein actuating comprises:

i. detecting, by the multi-touch input surface 206, the first plurality of contact points 204 associated with the finger contact of the fingertip 201, ii. calculating, by the graphical user interface, the first mask 202 for the first plurality of contact points 204 associated with the finger contact, wherein the first mask 202 is the closed shape, wherein the calculating is performed in the background without displaying the first mask 202, iii. detecting, by the multi-touch input surface 206 the second plurality of contact points 205 associated with the finger contact, wherein the second plurality of contact points 205 is caused by the change in the 3-dimensional shape of the fingertip 201, wherein the change in the 3-dimensional shape of the fingertip 201 is caused by the redistribution of touch pressure associated with an imminent motion of the fingertip 201, iv. calculating, by the graphical user interface, the second mask 203 for the second plurality of contact points 205 associated with the finger contact, wherein the second mask 203 is the closed shape, wherein calculating is performed in the background without displaying the second mask 203, v. determining, by the graphical user interface, an anticipated direction of the imminent motion of the fingertip 201 by comparing the second mask 203 to the first mask 202, and vi. translating, by the graphical user interface, the second point and the floating magnification window 102 based on the anticipated direction of the imminent motion of the fingertip 201; and E. calculating, by the graphical user interface, a distance between the first point 101 and the second point.

11. The non-transitory computer-readable storage medium of claim 10, wherein the computer-executable instructions further comprise:

A. displaying, by the graphical user interface:

i. a third point on the ultrasound image 103, wherein the third point is configured to translate with two dimensions of translational freedom upon actuation by the user, and ii. the floating magnification window 102, wherein the floating magnification window 102 is concentric with the third point and configured to:

a. match the translation of the third point, and b. display the magnification of the region of the ultrasound image 103 that is bounded by the floating magnification window 102, wherein displaying the magnification comprises;

I. scaling by the magnification coefficient 105 the height and the width of the copy 104 of the ultrasound image 103, and II. translating the copy 104 of the ultrasound mage 103 based on the magnification coefficient 105 to compensate for the scaling and maintain the position of the copy 104 of the ultrasound image 103 relative to the square frame;

B. actuating, bye the user, the third point to a third destination, wherein actuating is a gesture with continuous contact with the multi-touch input surface 206, wherein the floating magnification window 102 disappears when the user disengages the third point, wherein actuating comprises:

i. detecting, by the multi-touch input surface 206, the first plurality of contact points 204 associated with the finger contact of the fingertip 201, ii. calculating, by the graphical user interface, the first mask 202 for the first plurality of contact points 204 associated with the finger contact, wherein the first mask 202 is the closed shape, wherein the calculating is performed in the background without displaying the first mask 202, iii. detecting, by the multi-touch input surface 206, the second plurality of contact points 205 associated with the finger contact, wherein the second plurality of contact points 205 is caused by the change in the 3-dimensional shape of the fingertip 201, wherein the change in the 3-dimensional shape of the fingertip 201 is caused by the redistribution of touch pressure associated with an imminent motion of the fingertip 201, iv. calculating, by the graphical user interface, the second mask 203 for the second plurality of contact points 205 associated with the finger contact, wherein the second mask 203 is the closed shape, wherein calculating is performed in the background without displaying the second mask 203, v. determining, by the graphical user interface, an anticipated direction of the imminent motion of the fingertip 201 by comparing the second mask 203 to the first mask 202, and vi. translating, by the graphical user interface, the third point and the floating magnification window 102 based on the anticipated direction of the imminent motion of the fingertip 201; and C. calculating, by the graphical user interface, an angle formed by the first point 101, the second point, and the third point, wherein a vertex of the angle is the second point.

12. The non-transitory computer-readable storage medium of claim 10, wherein the computer-executable instructions further comprise:
   A. displaying, by the graphical user interface, an ellipse 401 on the ultrasound image 103,
      i. comprising a superior point, an inferior point, and a lateral point, wherein the superior point, the inferior point, and the lateral point are points on the ellipse, wherein the superior point is superior to all other points of the ellipse 401, the inferior point is inferior to all other points of the ellipse 401, and the lateral point is a maximum lateral distance from center of the ellipse 401,
      ii. wherein every point on the ellipse 401 is configured to be unresponsive to actuation by direct touch,
      iii. wherein a width of the ellipse 401 is configured to be scaled by a finger swipe gesture 402 only if an origin point of the finger swipe gesture 402 is not a point on the ellipse 401,
      iv. wherein the ellipse 401 is configured to be immutable after the width of the ellipse 401 has been scaled by the finger swipe gesture 402, and
      v. wherein displaying the ellipse 401 on the ultrasound image 103 comprises:
         a. scaling a height of the ellipse 401 to match the distance between the first point 101 and the second point, and
         b. rotating the scaled ellipse 401 to align the superior point to the first point 101 at the first destination and the inferior point to the second point at the second destination;
   B. detecting, by the graphical user interface, the finger swipe gesture 402; and
   C. scaling, by the graphical user interface, the width of the ellipse 401 based on one or more attributes of the finger swipe gesture 402.

13. The non-transitory computer-readable storage medium of claim 12, wherein the computer-executable instructions for scaling the width based on one or more attributes further comprise:
   A. defining the width of the ellipse as a proportion of a length of the swipe, wherein the proportion is less than or equal to one.

14. The non-transitory computer-readable storage medium of claim 12, wherein the computer-executable instructions for scaling the width based on one or more attributes further comprise:
   A. defining the width of the ellipse as a sum of the width of the ellipse and a proportion of a length of the swipe, wherein the proportion is less than or equal to one.

15. The non-transitory computer-readable storage medium of claim 12, wherein the computer-executable instructions for scaling the width based on one or more attributes further comprise:
   A. equating an x-coordinate of the lateral point to an x-coordinate of an end point of the finger swipe gesture 402.

16. The non-transitory computer-readable storage medium of claim 12, wherein the computer-executable instructions for scaling the width based on one or more attributes further comprise:
   A. equating a y-coordinate of the lateral point to a y-coordinate of an end point of the finger swipe gesture 402.

17. The non-transitory computer-readable storage medium of claim 12, wherein the computer-executable instructions for scaling the width based on one or more attributes further comprise:
   A. adding to an x-coordinate of the lateral point a difference between an x-coordinate of an end point of the finger swipe gesture 402 and an x-coordinate of the origin point.

18. The non-transitory computer-readable storage medium of claim 12, wherein the computer-executable instructions for scaling the width based on one or more attributes further comprise:
   A. adding to a y-coordinate of the lateral point a difference between a y-coordinate of an end point of the finger swipe gesture 402 and a y-coordinate of the origin point.

19. A system for taking medically precise measurements comprising:
   A. a mobile device comprising a processor, RAM, a multi-touch input surface 206, an I/O port configured to interface with a handheld ultrasound device, and a hard disk memory, wherein the hard disk memory comprises a graphical user interface, wherein the graphical user interface comprises:
      i. a distance-measuring module, comprising computer-executable instructions for:
         a. displaying:
            I. a first point 101 on an ultrasound image 103, wherein the first point 101 is configured to translate with two dimensions of translational freedom upon actuation by a user, and
            II. a floating magnification window 102, wherein displaying the floating magnification window 102 comprises calculating a square frame based on the first point 101, a size of an area of magnification a width of the multi-touch input surface 206, and a height of the multi-touch input surface 206, wherein the square frame is configured to crop a copy 104 of the ultrasound image 103, wherein the floating magnification window 102 is concentric with the first point 101 and configured to:
               1) match the translation of the first point 101, and
               2) display a magnification of a region of the ultrasound image 103 that is bounded by the floating magnification window 102, wherein displaying the magnification comprises:
                  A) scaling by a magnification coefficient 105 a height and a width of the copy 104 of the ultrasound image 103, and
                  B) translating the copy 104 of the ultrasound image 103 based on the magnification coefficient 105 to compensate for the scaling and maintain a position of the copy 104 of the ultrasound image 103 relative to the square frame,
         b. actuating, by the user, the first point 101 to a first destination, wherein actuating is a gesture with continuous contact with the multi-touch input surface 206, wherein the floating magnification window 102 disappears when the user disengages the first point 101, wherein actuating comprises:

I. detecting, by the multi-touch input surface 206, a first plurality of contact points 204 associated with a finger contact of a fingertip 201,
II. calculating a first mask 202 for the first plurality of contact points 204 associated with the finger contact, wherein the first mask 202 is a closed shape, wherein the calculating is performed in the background without displaying the first mask 202,
III. detecting, by the multi-touch input surface 206, a second plurality of contact points 205 associated with the finger contact, wherein the second plurality of contact points 205 is caused by a change in a 3-dimensional shape of the fingertip 201, wherein the change in the 3-dimensional shape of the fingertip 201 is caused by a redistribution of touch pressure associated with an imminent motion of the fingertip 201,
IV. calculating a second mask 203 for the second plurality of contact points 205 associated with the finger contact, wherein the second mask 203 is a closed shape, wherein calculating is performed in the background without displaying the second mask 203,
V. determining an anticipated direction of the imminent motion of the fingertip 201 by comparing the second mask 203 to the first mask 202, and
VI. translating the first point 101 and the floating magnification window 102 based on the anticipated direction of the imminent motion of the fingertip 201,
c. displaying:
I. second point on the ultrasound image 103, wherein the second point is configured to translate with two dimensions of translational freedom upon actuation by the user, and
II. the floating magnification window 102, wherein the floating magnification window 102 is concentric with the second point and configured to:
1) match the translation of the second point, and
2) display the magnification of the region of the ultrasound image 103 that is bounded by the floating magnification window 102, wherein displaying the magnification comprises:
A) scaling by the magnification coefficient 105 the height and the width of the copy 104 of the ultrasound image 103, and
B) translating the copy 104 of the ultrasound image 103 based on the magnification coefficient 105 to compensate for the scaling and maintain the position of the copy 104 of the ultrasound image 103 relative to the square frame,
d. actuating, by the user, the second point to a second destination, wherein actuating is a gesture with continuous contact with the multi-touch input surface 206, wherein the floating magnification window 102 disappears when the user disengages the second point, wherein actuating comprises:
I. detecting, by the multi-touch input surface 206, the first plurality of contact points 204 associated with the finger contact of the fingertip 201,
II. calculating the first mask 202 for the first plurality of contact points 204 associated with the finger contact, wherein the first mask 202 is the closed shape, wherein the calculating is performed in the background without displaying the first mask 202,
III. detecting, by the multi-touch input surface 206, the second plurality of contact points 205 associated with the finger contact, wherein the second plurality of contact points 205 is caused by the change in the 3-dimensional shape of the fingertip 201, wherein the change in the 3-dimensional shape of the fingertip 201 is caused by the redistribution of touch pressure associated with an imminent motion of the fingertip 201,
IV. calculating the second mask 203 for the second plurality of contact points 205 associated with the finger contact, wherein the second mask 203 is the closed shape, wherein calculating is performed in the background without displaying the second mask 203,
V. determining an anticipated direction of the imminent motion of the fingertip 201 by comparing the second mask 203 to the first mask 202, and
VI. translating the second point and the floating magnification window 102 based on the anticipated direction of the imminent motion of the fingertip 201, and
e. calculating a distance between the first point 101 and the second point,
ii. an angle-measuring module, comprising computer-executable instructions for the distance-measuring module and computer-executable instructions for:
a. displaying:
I. a third point on the ultrasound image 103, wherein the third point is configured to translate with two dimensions of translational freedom upon actuation by the user, and
II. the floating magnification window 102, wherein the floating magnification window 102 is concentric with the third point and configured to:
1) match the translation of the third point, and
2) display the magnification of the region of the ultrasound image 103 that is bounded by the floating magnification window 102, wherein displaying the magnification comprises:
A) scaling by the magnification coefficient 105 the height and the width of the copy 104 of the ultrasound image 103, and
B) translating the copy 104 of the ultrasound image 103 based on the magnification coefficient 105 to compensate for the scaling and maintain the position of the copy 104 of the ultrasound image 103 relative to the square frame,
b. actuating, by the user, the third point to a third destination, wherein actuating is a gesture with continuous contact with the multi-touch input surface 206, wherein the floating magnification window 102 disappears when the user disengages the third point, wherein actuating comprises:
I. detecting, by the multi-touch input surface 206, the first plurality of contact points 204 associated with the finger contact of the fingertip 201,
II. calculating the first mask 202 for the first plurality of contact points 204 associated with the finger contact, wherein the first mask 202 is the closed shape, wherein the calculating is performed in the background without displaying the first mask 202, III. detecting, by the multi-touch input surface 206, the second plurality of contact points 205 associated with the finger contact, wherein the second plurality of contact points 205 is caused by the change in the 3-dimensional shape of the fingertip 201 wherein the change in the 3-dimensional shape of the fingertip 201 is caused by the redistribution of touch pressure associated with an imminent motion of the fingertip 201, IV. calculating the second mask 203 for the second plurality of contact points 205 associated with the finger contact, wherein the second mask 203 is the closed shape, wherein calculating is performed in the background without displaying the second mask 203, V. determining an anticipated direction of the imminent motion of the fingertip 201 by comparing the second mask 203 to the first mask 202, and VI. translating the third point and the floating magnification window 102 based on the anticipated direction of the imminent motion of the fingertip 201, and c. calculating an angle formed by the first point 101, the second point, and the third point, wherein a vertex of the angle is the second point, and iii. an ellipse-generating module, comprising computer-executable instructions for the distance-measuring module and computer-executable instructions for:

a. displaying an ellipse 401 on the ultrasound image 103,

I. comprising a superior point, an inferior point, and a lateral point, wherein the superior point, the inferior point, and the lateral point are points on the ellipse, wherein the superior point is superior to all other points of the ellipse 401, the inferior point is inferior to all other points of the ellipse 401, and the lateral point is a maximum lateral distance from center of the ellipse 401, II. wherein every point on the ellipse 401 is configured to be unresponsive to actuation by direct touch, III. wherein a width of the ellipse 401 is configured to be scaled by a finger swipe gesture 402 only if an origin point of the finger swipe gesture 402 is not a point on the ellipse 401, IV. wherein the ellipse 401 is configured to be immutable after the width of the ellipse 401 has been scaled by the finger swipe gesture 402, and V. wherein displaying the ellipse 401 on the ultrasound image 103 comprises:

1) scaling a height of the ellipse 401 to match the distance between the first point 101 and the second point, and 2) rotating the scaled ellipse 401 to align the superior point to the first point 101 at the first destination and the inferior point to the second point at the second destination, b. detecting, by the graphical user interface, the finger swipe gesture 402, and c. scaling the width of the ellipse 401 based on one or more attributes of the finger swipe gesture 402; and B. the handheld ultrasound device.

20. The system of claim 19, wherein the computer-executable instructions for scaling the width based on one or more attributes further comprise one or more of:

A. defining the width of the ellipse as a proportion of a length of the swipe, wherein the proportion is less than or equal to one;

B. defining the width of the ellipse as a sum of the width of the ellipse and a proportion of a length of the swipe, wherein the proportion is less than or equal to one;

C. equating an x-coordinate of the lateral point to an x-coordinate of an end point of the finger swipe gesture 402;

D. equating a y-coordinate of the lateral point to a y-coordinate of an end point of the finger swipe gesture 402;

E. adding to an x-coordinate of the lateral point a difference between an x-coordinate of an end point of the finger swipe gesture 402 and an x-coordinate of the origin point; and F. adding to a y-coordinate of the lateral point a difference between a y-coordinate of an end point of the finger swipe gesture 402 and a y-coordinate of the origin point.

\* \* \* \* \*